United States Patent
Paterek

(10) Patent No.: US 6,887,692 B2
(45) Date of Patent: May 3, 2005

(54) METHOD AND APPARATUS FOR HYDROGEN PRODUCTION FROM ORGANIC WASTES AND MANURE

(75) Inventor: James Robert Paterek, Naperville, IL (US)

(73) Assignee: Gas Technology Institute, Des Plaines, IL (US)

( * ) Notice: Subject to any disclaimer, the term of this patent is extended or adjusted under 35 U.S.C. 154(b) by 309 days.

(21) Appl. No.: 10/322,087

(22) Filed: Dec. 17, 2002

(65) Prior Publication Data

US 2004/0115782 A1 Jun. 17, 2004

(51) Int. Cl.$^7$ .............................. C12P 3/00; C12M 1/00
(52) U.S. Cl. ................ 435/168; 435/290.1; 435/290.4; 435/292.1
(58) Field of Search ............................. 435/168, 290.1, 435/290.4, 292.1

(56) References Cited

U.S. PATENT DOCUMENTS

| | | | |
|---|---|---|---|
| 4,022,665 A | 5/1977 | Ghosh et al. | |
| 4,268,279 A | 5/1981 | Shindo et al. | |
| 4,316,961 A | 2/1982 | Klass et al. | |
| 4,318,993 A | 3/1982 | Ghosh et al. | |
| 4,329,428 A | 5/1982 | Ghosh et al. | |
| 4,424,064 A | 1/1984 | Klass et al. | |
| 4,468,463 A * | 8/1984 | Arsovic | 435/290.4 |
| 4,696,746 A | 9/1987 | Ghosh et al. | |
| 4,735,724 A | 4/1988 | Chynoweth et al. | |
| 4,966,699 A | 10/1990 | Sasaki et al. | |
| 5,198,110 A | 3/1993 | Hanai et al. | |
| 5,500,123 A | 3/1996 | Srivastava | |
| 5,693,230 A | 12/1997 | Asher | |
| 5,782,950 A * | 7/1998 | Kanitz et al. | 71/10 |
| 5,821,111 A * | 10/1998 | Grady et al. | 435/252.5 |
| 6,342,378 B1 * | 1/2002 | Zhang et al. | 435/168 |

* cited by examiner

Primary Examiner—Herbert J. Lilling
(74) Attorney, Agent, or Firm—Mark E. Fejer

(57) ABSTRACT

A method for hydrogen production from biodegradable feedstocks in which a feedstock having at least one biodegradable solid is introduced into a first stage anaerobic bioreactor operating at thermophilic conditions to form a liquid effluent which includes fatty acids. The liquid effluent is transferred through a plurality of hollow semipermeable fibers disposed in a second stage anaerobic bioreactor having a light transmitting wall, which hollow semipermeable fibers have an outer surface coated with a biofilm of photosynthetic bacteria, which photosynthetic bacteria, using the nutrients in the hollow fibers and the incoming light, generates hydrogen.

17 Claims, 2 Drawing Sheets

METHOD AND APPARATUS FOR HYDROGEN PRODUCTION FROM ORGANIC WASTES AND MANURE

BACKGROUND OF THE INVENTION

1. Field of the Invention

This invention relates to two-phase anaerobic digestion of biodegradable feedstocks, such as organic wastes and manure. More particularly, this invention relates to a method and apparatus for two-phase anaerobic digestion of organic wastes, such as manure from large animal production, food processing wastes, as well as energy crops, e.g. grasses, corn etc. for producing hydrogen gas for use in energy production in which the second anaerobic digestion phase is carried out in a bioreactor vessel utilizing hollow semipermeable fibers in which the liquid effluent from the first anaerobic phase is transmitted into the hollow semipermeable fibers, which then passes through the semipermeable walls of the fibers for processing by photosynthetic bacterial cultures disposed in the second phase bioreactor vessel and surrounding the fibers. The hydrogen gas generated can be used in conjunction with fuel cell technology to generate electricity on the farms and factories producing the wastes, to replace or supplement the needs of the facilities.

The high-organic wastes generated by these farms and factories are now a liability for them and in many cases incur a cost for disposal. In the case of farms and large animal production facilities, the wastes are discharged to a lagoon for anaerobic digestion to proceed until land application is executed. However, lagoons release a number of gases, including greenhouse gases, methane and carbon dioxide to the atmosphere, which increases their negative impact to the environment. This invention converts this liability into an asset.

2. Description of Related Art

The production of methane and other usable gases by anaerobic digestion of various organic wastes is well-known. The organic feed mixture which provides the substrate for anaerobic biodegradation may comprise a wide variety of organic carbon sources, ranging from raw sewage sludge to municipal refuse, or biomass material such as plants and crop wastes. Anaerobic digestion of organic feedstocks generally involves hydrolysis fermentation of organic feedstocks to acidic intermediates by acid forming bacteria and conversion of the acidic intermediates to useful gases, such as methane, by methane-producing organisms. Many digester designs, feedstocks mixtures and additives have been proposed to increase the methane yield from anaerobic digestion and to provide greater conversion efficiency of organic materials to useful products.

Early designs of sewage digesters attempted to biodegrade sewage sludge for the purposes of sludge volume and odor reduction in an unmixed digester, but they were generally unsuccessful because they failed to provide adequate control of solids inventory, and they developed serious problems such as scum buildup, temperature fluctuations, unequal microbial activity and limited contact between the organic material and the bacteria. Most newer anaerobic digesters for biological conversion of biomass and community wastes are continuously stirred tank reactors, which provide complete mixing of the reactor contents. Solids and hydraulic retention times are equal in continuously stirred tank reactors and both hydrolysis fermentation reactions converting organic materials to acidic intermediates and methane-producing reactions converting acidic intermediates to methane and other gases occur throughout the reactor.

Many organic feedstocks have a relatively low suspended solids content, for example less than about 10 percent suspended solids. The high water content of these types of organic feedstocks causes washout of feed solids and microorganisms from continuously stirred tank reactors at high feed loadings due to high dilution rates. Washout of feed solids and microorganisms results in reduced conversion efficiency and unstable digester conditions. Shorter feed solids retention times in the digester, washout of slow-growing methanogenic bacteria and accumulation of inhibitory acidic fermentation products contribute to low conversion efficiency and reduced methane production.

Anaerobic filter-type reactors promote the retention of bacteria in the digester by attaching bacteria to fixed inert materials in the digester. Anaerobic filter-type digesters are also limited to primarily liquid feedstocks containing less than about 1 percent solids because they become plugged when solids concentration in the digester increases due to higher solids loading or accumulation of solids over longer periods of operation.

U.S. Pat. No. 4,329,428 teaches production of methane gas in higher yields and at higher rates by thermophilic and mesophilic anaerobic digestion of a mixture of plant material of terrestrial or aquatic origin and organic waste. U.S. Pat. No. 4,424,064 teaches production of methane gas with higher yields and at higher rates by thermophilic or mesophilic anaerobic digestion of aquatic plant material, at least a portion or all of which has been grown in organically polluted water. U.S. Pat. No. 4,316,961 teaches higher yields of methane gas at higher rates by thermophilic or mesophilic anaerobic digestion of plant material and/or organic waste of normally low biodegradability in the presence of an extract of different plant material.

Separated two phase anaerobic digestion processes have been found to enhance the conversion efficiency. See, for example, U.S. Pat. No. 4,318,993. In an acid first phase, the microbial population and operating conditions are selected to promote the conversion of organic carbonaceous matter to volatile fatty acids of low molecular weight. The volatile fatty acids remain solubilized in the liquid portion of the digester contents. The liquid and solid effluent from the acid phase is conveyed to a methane second phase, where methanogenic microorganisms convert the volatile fatty acids to product gas composed primarily of methane and carbon dioxide. Product gas is removed from the methane phase and processed, or scrubbed, to separate the methane component which is drawn off as pipeline gas. U.S. Pat. No. 4,022,665 teaches certain specific operating conditions for a two phase anaerobic digestion process in separated vessels which promotes more efficient conversion of organic material.

The use of hollow semipermeable fibers in connection with the processing and treatment of various liquids is well documented in the prior art. U.S. Pat. No. 4,268,279 teaches microporous hollow fibers with a liquid in the fiber lumen and a fluid outside the fiber allowing gaseous components to transfer through the microporous fiber to the inside or outside of the fiber. U.S. Pat. No. 4,966,699 teaches a hollow fiber membrane fluid processor providing counter current flow of fluid in the fiber lumen and the fluid surrounding the outside of the fibers from one end of the fiber bundle to the other. U.S. Pat. No. 5,198,110 teaches a bundle of permselective hollow fibers having a plurality of filaments extending substantially lengthwise over the length of the exterior of each fiber. U.S. Pat. No. 5,693,230 teaches a hollow fiber contactor and process having forced circulation with entry of fluid to be processed through the open ended lumen of a porous input hollow fiber having its opposite end closed and exit of treated fluid through the open ended lumen of an adjacent or nearby porous output hollow fiber having its opposite end closed. In the contactor, the fluid to be processed passes through the porous wall of an input hollow fiber, contacting a treatment medium and forming a treated fluid which passes through the porous wall of an output hollow fiber and exits the contactor.

SUMMARY OF THE INVENTION

It is one object of this invention to provide a method and system for producing hydrogen from carbonaceous materials such as organic wastes, food processing wastes and energy crops.

It is another object of this invention to provide a method and system using carbonaceous materials for producing hydrogen suitable for direct use in fuel cell applications.

It is another object of this invention to provide a method and system which provides beneficial disposition of the high-organic wastes generated by farms and industry.

These and other objects of this invention are addressed by a method for hydrogen production from biodegradable feedstocks in which a feedstock comprising at least one biodegradable solid is introduced into a first stage anaerobic bioreactor operating at thermophilic conditions, resulting in formation of a liquid effluent. The liquid effluent is transferred into and through a plurality of hollow semipermeable fibers having an outer surface coated with a biofilm comprising photosynthetic bacteria, which hollow semipermeable fibers are disposed in a second stage anaerobic bioreactor having a light transmitting wall through which light is transmitted, resulting in the generation of hydrogen gas. The hydrogen gas is then exhausted from the second stage anaerobic bioreactor, possibly for direct use in a fuel cell application or storage in a hydrogen facility.

The system for producing hydrogen in accordance with the method of this invention is a two-phase anaerobic digestion system comprising a first stage anaerobic acid-phase bioreactor vessel and a second stage anaerobic hydrogenogenic photosynthetic bioreactor vessel in fluid communication with the first stage anaerobic bioreactor vessel. The first stage anaerobic bioreactor vessel comprises a feedstock inlet and a liquid effluent outlet. The second stage anaerobic bioreactor vessel comprises at least one light transmitting outer wall and forms a liquid effluent inlet that is in fluid communication with the liquid effluent outlet of the first stage anaerobic bioreactor vessel and a hydrogen gas outlet. Disposed within the second stage anaerobic bioreactor vessel is a plurality of hollow semipermeable fibers that are adapted to receive liquid effluent from the liquid effluent inlet. At least one photosynthetic bacterial culture is disposed within the second stage anaerobic bioreactor vessel but external to the plurality of hollow semipermeable fibers. As a result, the photosynthetic bacterial culture forms a biofilm on the outer surfaces of the hollow semipermeable fibers. Hydrogen gas formed by the photosynthetic processing of the liquid effluent by the bacterial culture is exhausted through a hydrogen gas outlet formed by the second stage anaerobic bioreactor vessel wall.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
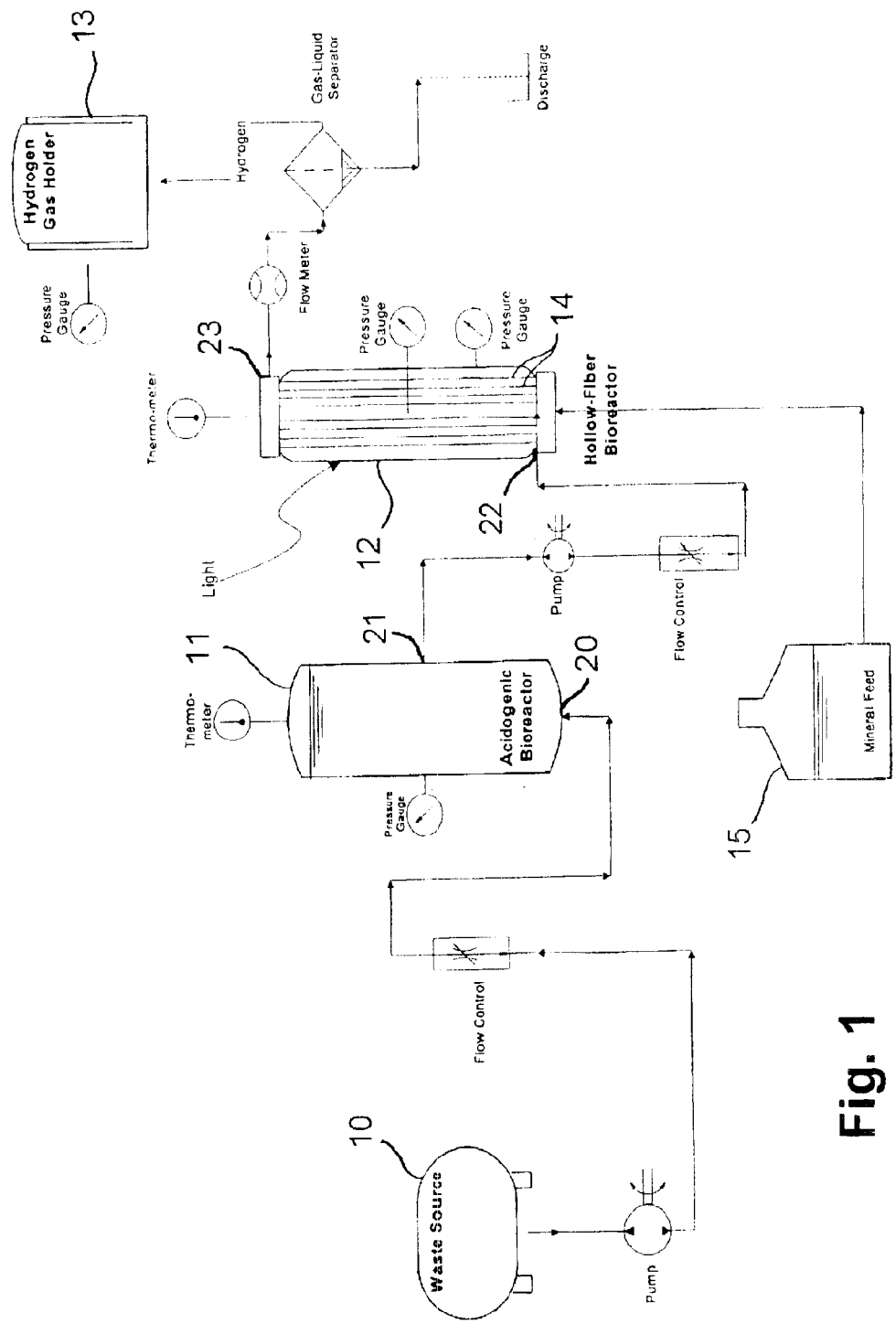
FIG. 1 is a diagram of a two stage anaerobic digestion system for converting organic waste and manures to hydrogen in accordance with one embodiment of this invention.

FIG. 1 is a diagram showing a two stage anaerobic digestion system for performing the method of this invention. The system comprises a first stage anaerobic bioreactor vessel 11 having a feedstock inlet 20 in fluid communication with a waste source 10 and a liquid effluent outlet 21 in fluid communication with liquid effluent inlet of the second stage anaerobic bioreactor vessel 12. In accordance with one embodiment of this invention, both the first stage anaerobic bioreactor and the second stage anaerobic bioreactor are constantly stirred tank reactors.

Second stage anaerobic bioreactor vessel 12 is a photosynthetic bioreactor comprising an outer wall that is light transmissive. In accordance with one embodiment of this invention, the outer wall is transparent; in accordance with another embodiment of this invention, the outer wall is translucent. Disposed within the second stage anaerobic bioreactor vessel 12 is a plurality of hollow semipermeable fibers 14 suitably arranged to receive the liquid effluent entering the bioreactor vessel through liquid effluent inlet 22. Hydrogen gas produced in the second stage anaerobic bioreactor vessel 12 is exhausted through outlet 23. In accordance with one embodiment of this invention, the hydrogen gas produced in the second stage anaerobic bioreactor vessel 12 is transmitted to storage means such as hydrogen storage tank 13 for storage until needed. Alternatively, given the fact that the hydrogen produced in accordance with the method of this invention is substantially free of contaminants that might detrimentally affect the operation of hydrogen consuming applications, the hydrogen gas may be transmitted directly from the second stage anaerobic bioreactor vessel to such an application, such as a fuel cell, in which it is consumed.

Figure 2:
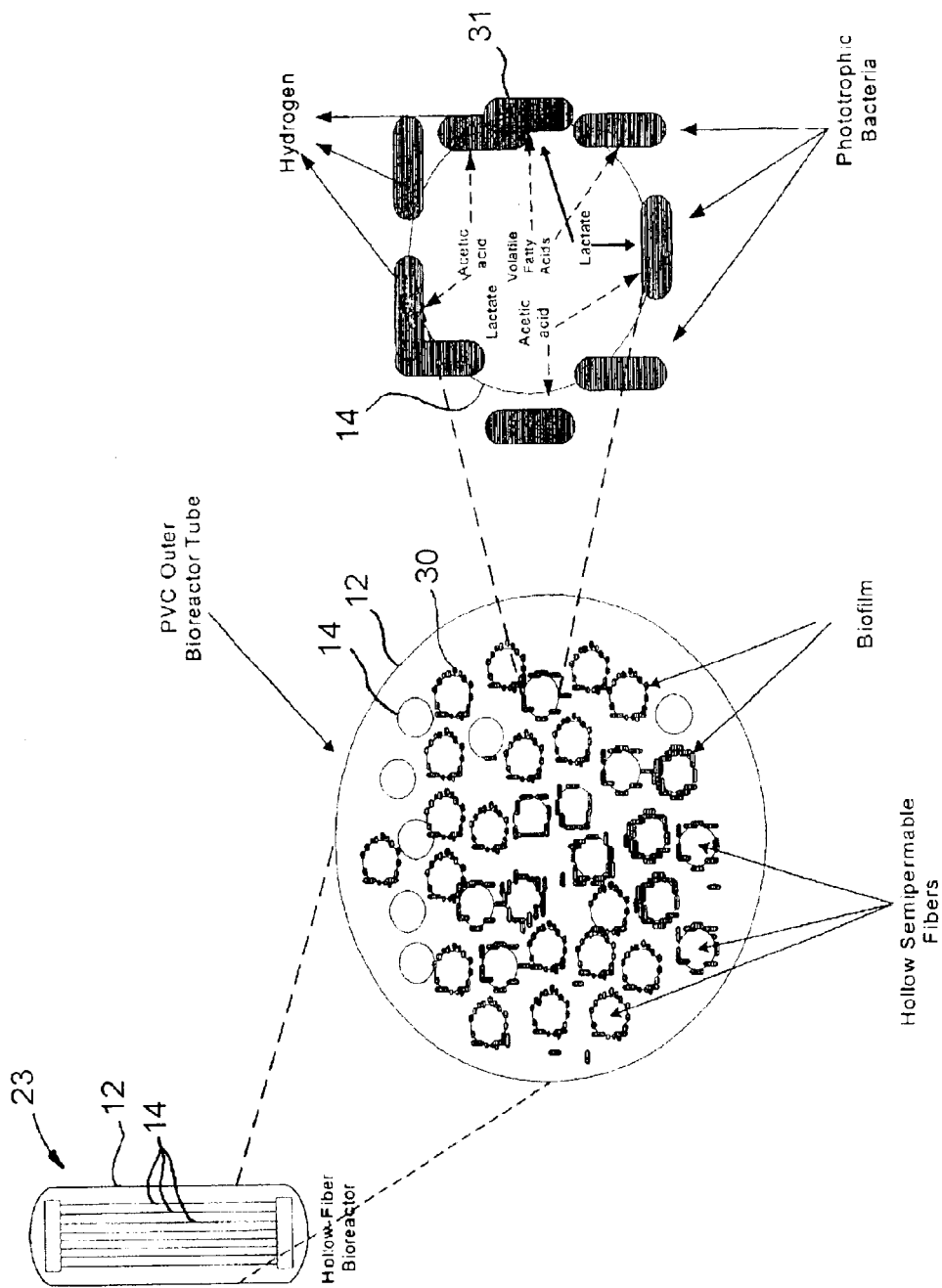
FIG. 2 is a diagrammatic representation of the configuration of the second stage anaerobic bioreactor vessel in accordance with one embodiment of this invention.

Disposed within the second stage anaerobic bioreactor vessel 12 is a plurality of hollow semipermeable fibers 14 arranged to enable liquid effluent entering second stage bioreactor vessel 12 through inlet 22 to flow into the fiber lumen. Disposed within the second stage anaerobic bioreactor vessel 12 in the space surrounding the hollow semipermeable fibers 14 is at least one photosynthetic bacterial culture 31 as shown in FIG. 2. During operation of the second stage anaerobic bioreactor in accordance with the method of this invention, the photosynthetic bacteria form a biofilm 30 on the outer surfaces of the hollow semipermeable fibers. As used herein, the term "photosynthetic bacterial culture" refers to a bacterial culture that employs photosynthesis as a means for processing feed materials. Examples of photosynthetic bacteria suitable for use in the method and apparatus include *Rubrivivax gelatinosus, Rhodopseudomonas palustris* and *Rhodospirillum rubrum*.

Suitable hollow semipermeable fibers for use in this invention have side walls with a viscosity normalized permeance of at least about $10^{-3}$–$10^{-4}$ ft$^2$/sec, preferably greater than about $5 \times 10^{-3}$ ft$^2$/sec, and most preferably greater than about $5 \times 10^{-4}$ ft$^2$/sec, and in all cases have pores small enough to prevent the passage of the photosynthetic bacteria into the lumen of the fibers. Generally, the thickness of the porous walls of the hollow semipermeable fibers is about 40 to about 60 percent of their outside diameters. The hollow semipermeable fibers may be made of any suitable material which is inert under the conditions of operation of the second stage anaerobic bioreactor, that is not chemically reactive with the liquid effluent flowing through the lumen or the photosynthetic bacteria surrounding the outside of the fibers. Examples of suitable materials include hydrophilic polymeric materials.

Hydrogen is produced in accordance with one embodiment of the method of this invention by introducing a feedstock comprising biodegradable solids into a first stage anaerobic bioreactor 11. Suitable feedstocks include, but are not limited to, manures, food processing wastes, energy crops, such as corn and grasses, and the like. Anaerobic fermentation of the feedstock in the first stage anaerobic bioreactor 11 is carried out under thermophilic conditions, preferably at temperatures in the range of about 45° C. to about 65° C., to kill pathogenic bacteria and protozoa, resulting in the generation of a Class A biosolid (based upon Environmental Protection Agency (EPA) Protocol 503A) that can be land applied or marketed as a soil supplement. To prevent the establishment of methanogenic bacteria, retention times for feedstock within the first stage anaerobic bioreactor should be as short as possible, preferably in the range of about 24 to 48 hours. Suitable microorganisms for use in the first stage anaerobic bioreactor are microorganisms that ferment the feedstock to fatty acids and other small carbon compounds. Such microorganisms can be indigenous to the waste, such as manure, or obtained from commercial sources. Examples of such microorganisms include *Clostridium, Bacillus, Bacteroides* and others that generate volatile fatty acids such as acetic, butyric and propionic acids and lactic acid. In accordance with one preferred embodiment of this invention, the first stage anaerobic bioreactor 11 is operated with zero-headspace or near zero-headspace to maintain the gases produced therein ($H_2$, $CO_2$ $H_2S$) in solution for transfer to the photosynthetic bacterial biofilm in the second stage hydrogenogenic reactor 12.

The liquid fraction of the effluent from the first stage anaerobic bioreactor is transferred through the hollow fibers 14 disposed in the second stage anaerobic bioreactor to allow the transfer of the fatty acids, such as acetic and lactic acids, produced in the acidogenic first stage anaerobic bioreactor, to the photosynthetic bacterial biofilm. The photosynthetic bacteria utilize the nutrients passing through the walls of the hollow semipermeable fibers for growth and, along with the incoming light, generate hydrogen. The photosynthetic bacteria utilized in the method and system of this invention may be either an axenic culture or a mixed culture.

In accordance with one embodiment of this invention, if additional complex polymeric carbon compounds disposed in the liquid effluent from the first stage anaerobic bioreactor that could continue to digest in the first stage bioreactor to generate additional fatty acids and other small fermentation products that the photosynthetic bacteria can use for growth and/or hydrogen generation remain in the hollow semipermeable fibers of the second stage anaerobic bioreactor, such compounds may be recycled to the first stage anaerobic bioreactor for further digestion.

In accordance with one embodiment of this invention, to enable recovery of the biosolids, the biosolids formed in both stages are dewatered.

The benefits of the method and system of this invention will be apparent to those skilled in the art. In particular, the method and system of this invention converts a high percent of organic wastes, such as manures, into hydrogen that can be used in a fuel cell for the generation of electricity. The waste stream is converted without direct release of greenhouse gases, such as methane or carbon dioxide, in the first stage anaerobic bioreactor. The waste stream from the second stage anaerobic bioreactor generates no methane and a minimal amount of carbon dioxide where a major proportion thereof is trapped in the biomass of the photosynthetic bacteria. The solids generated from both bioreactors meets or exceeds the criteria of Class A Biosolids as defined by EPA 503A.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A method for hydrogen production from biodegradable feedstocks comprising the steps of:
   introducing a feedstock comprising at least one biodegradable solid into a first stage anaerobic bioreactor operating at thermophilic conditions, forming a liquid effluent;
   transferring said liquid effluent through a plurality of hollow semipermeable fibers disposed in a second stage anaerobic bioreactor having a light transmitting wall through which light is transmitted, said hollow semipermeable fibers having an outer surface coated with a biofilm comprising photosynthetic bacteria, forming hydrogen gas; and
   exhausting said hydrogen gas from said second stage anaerobic bioreactor.

2. A method in accordance with claim 1, wherein said first stage anaerobic bioreactor is operated with substantially zero-headspace.

3. A method in accordance with claim 1, wherein said first stage anaerobic bioreactor is operated at a temperature in a range of about 45° C. to about 65° C.

4. A method in accordance with claim 1, wherein said liquid effluent comprises at least one fatty acid.

5. A method in accordance with claim 1, wherein at least a portion of said liquid effluent in said hollow semipermeable fibers is recycled to said first stage anaerobic bioreactor.

6. A method in accordance with claim 1, wherein said first stage anaerobic bioreactor and said second stage anaerobic bioreactor are constantly stirred tank reactors.

7. A method in accordance with claim 1, wherein said biodegradable solids comprise a material selected from the group consisting of manure, food processing wastes, energy crops and mixtures thereof.

8. A method in accordance with claim 1, wherein said photosynthetic bacteria comprise at least one of an axenic culture and a mixed culture.

9. A method in accordance with claim 1, wherein said first stage anaerobic bioreactor is an acidogenic bioreactor.

10. A method in accordance with claim 1, wherein a portion of said liquid effluent in said hollow semipermeable fibers is dewatered, resulting in formation of biosolids.

11. A method in accordance with claim 1, wherein said first stage anaerobic bioreactor generates biosolids.

12. A system for producing hydrogen comprising:
   a first stage anaerobic bioreactor vessel having a feedstock inlet and a liquid effluent outlet;
   a second stage anaerobic bioreactor vessel having a light transmitting outer wall, a liquid effluent inlet in fluid communication with said liquid effluent outlet and a hydrogen gas outlet;

a plurality of hollow semipermeable fibers disposed in said second stage bioreactor vessel adapted to receive liquid effluent from said liquid effluent inlet; and at least one photosynthetic bacteria disposed in said second stage anaerobic bioreactor and external to said plurality of hollow semipermeable fibers.

13. A system in accordance with claim 12, wherein said first stage anaerobic bioreactor is operable at substantially zero-headspace.

14. A system in accordance with claim 12 further comprising recycle means for recycling a portion of liquid effluent disposed in said second stage anaerobic bioreactor into said first stage anaerobic bioreactor.

15. A system in accordance with claim 12, wherein said at least one photosynthetic bacteria is an axenic culture.

16. A system in accordance with claim 12, wherein said at least one photosynthetic bacteria is a mixed culture.

17. A system in accordance with claim 12, wherein said first stage anaerobic bioreactor and said second stage anaerobic bioreactor are constantly stirred tank reactors.

* * * * *